United States Patent [19]

Berg

[11] Patent Number: 5,069,756

[45] Date of Patent: Dec. 3, 1991

[54] SEPARATION OF CYCLOHEXANE FROM CYCLOHEXENE BY AZEOTROPIC OR EXTRACTIVE DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 618,304

[22] Filed: Nov. 26, 1990

[51] Int. Cl.$^5$ .................. B01D 3/36; B01D 3/40; C07C 7/00

[52] U.S. Cl. ..................................... 203/51; 203/56; 203/58; 203/60; 203/62; 203/63; 203/64; 585/860; 585/864; 585/865; 585/866

[58] Field of Search ............... 203/63, 64, 62, 60, 203/56, 51, 58; 585/803, 860, 865, 866, 800, 809, 864; 208/313

[56] References Cited

U.S. PATENT DOCUMENTS

| 2,302,608 | 11/1942 | Field | 588/864 |
|---|---|---|---|
| 2,356,240 | 8/1944 | Hamlin | 203/63 |
| 2,517,839 | 8/1950 | Carnell | 585/803 |
| 2,909,576 | 10/1959 | Fenske | 585/803 |
| 3,673,081 | 6/1972 | Preusser et al. | 203/58 |
| 4,336,110 | 6/1982 | Reimer | 203/60 |
| 4,948,472 | 8/1990 | Lee et al. | 203/70 |

FOREIGN PATENT DOCUMENTS 52-5733  1/1977  Japan .................. 203/58

Primary Examiner—Wilbur Bascomb, Jr.

[57] ABSTRACT

Cyclohexane cannot be readily separated from cyclohexene by conventional distillation or rectification because of the close proximity of their boiling points. Cyclohexane can be separated from cyclohexene by azeotropic or extractive distillation. Typical examples of effective agents are: for azeotropic; ethylene glycol methyl ether and n-butanol; for extractive; propylene glycol methyl ether and diacetone alcohol.

2 Claims, No Drawings

SEPARATION OF CYCLOHEXANE FROM CYCLOHEXENE BY AZEOTROPIC OR EXTRACTIVE DISTILLATION

FIELD OF THE INVENTION

This invention relates to a method for separating cyclohexane from cyclohexene using certain organic liquids as the agent in azeotropic and extractive distillation.

DESCRIPTION OF THE PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling compound. This usually requires that the extractive agent boil twenty Centigrade degrees or more above the lowest boiling compound.

At the bottom of a continuous column, the less volatile components of the close boiling mixture and the extractive agent are continuously removed from the column. The usual methods of separation of these two components are the use of another rectification column, cooling and phase separation or solvent extraction.

Extractive distillation typically requires the addition of an equal amount to twice as much extractive agent as the cyclohexane-cyclohexene on each plate of the rectification column. The extractive agent should be heated to about the same temperature as the plate into which it is introduced. Thus extractive distillation imposes an additional heat requirement on the column as well as somewhat larger plates. However this is less than the increase caused by the additional agents requires if the separation is done by azeotropic distillation. Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. It is also desirable that the extractive agent be miscible with the acetic acid otherwise it will form a two-phase azeotrope with the cyclohexene in the recovery column and some other method of separation will have to be employed.

A recent commercial process has been developed to produce cyclohexanol by the air oxidation of cyclohexane. The process yields two by-products however. In the first step, the cyclohexane is oxidized to cyclohexene which is then oxidized again to a mixture of cyclohexanone and cyclohexanol. The reaction does not go to completion and some unreacted cyclohexane, B.P. +81° C. and cyclohexene, B.P.=83° C. remains and so these two remain to be recovered for recycle. They boil only two Celcius degrees apart and the relative volatility of cyclohexane to cyclohexene is 1.07.

TABLE 1

| Plates Required To Effect Separation Of 99% Purity | | |
|---|---|---|
| Relative Volatility | Theoretical Plates | Actual Plates, 75% Efficiency |
| 1.07 | 136 | 187 |
| 125 | 52 | 69 |
| 1.35 | 31 | 41 |
| 1.50 | 23 | 31 |
| 2.0 | 14 | 19 |
| 2.35 | 11 | 15 |

Table 1 shows that to separate a mixture having a relative volatility of 1.07, such as cyclohexane and cyclohexene, 136 theoretical plates or 187 actual plates would be required to separate it in 99% purity. If the relative volatility could be improved to 1.35, only 41 actual plates would be required and with a relative volatility of 2.35, only eleven actual plates are needed.

Extractive distillation would be an attractive method of effecting the separation of cyclohexane from cyclohexene if agents can be found that (1) will increase the relative volatility of one from the other and (2) are easy to recover from the cyclohexene being extracted, that is, form no azeotrope with cyclohexene and boil sufficienlty above it to make separation possible with only a few plates.

Azeotropic distillation would be another attractive method of effecting the separation of cyclohexane from cyclohexene if agents can be found that will enhance the relative volatility of these two.

OBJECTIVE OF THE INVENTION

The object of this invention is to provide a process or method of extractive or azeotropic distillation that will enhance the relative volatility of cyclohexane to cyclohexene in their separation in a rectification column. It is a further object of this invention to identify organic compounds which in addition to the above constraints, are stable, can be separated from the cyclohexane or cyclohexene being extracted by rectification with relatively few plates and can be recycled and reused with little decomposition.

TABLE 2

| Effective Agents For Separating Cyclohexane From Cyclohexene By Azeotropic Distillation | |
|---|---|
| Compounds | Relative Volatility |
| None | 1.07 |
| n-Propanol | 1.43 |
| Ethanol | 1.39 |
| n-Butanol | 2.01 |
| Ethylene glycol methyl ether | 2.33 |

TABLE 3

| Ineffective Agents for Separating Cyclohexane From Cyclohexene By Azeotropic Distillation | |
|---|---|
| Methanol | Isopropanol |
| Isopropanol, Dimethylacetamide | Isobutanol |
| t-Butanol | t-Amyl alcohol |

TABLE 4

Data From Run Made In Rectification Column - Cyclohexane From Cyclohexene By Azeotropic Distillation

| Agent | Column | Time hrs. | Weight % n-Butanol | Weight % Cyclohexane | Weight % Cyclohexene | Relative Volatility |
|---|---|---|---|---|---|---|
| n-Butanol | Overhead | 1 | 58.9 | 34.2 | 6.9 | 1.85 |
|  | Bottoms |  | 1.1 | 5.2 | 93.7 |  |
| n-Butanol | Overhead | 4 | 61.4 | 34.8 | 3.8 | 2.0 |
|  | Bottoms |  | 4.4 | 5.2 | 90.4 |  |

TABLE 5

Effective Agents For Separating Cyclohexane From Cyclohexene By Extractive Distillation

| Compounds | Relative Volatility |
|---|---|
| None | 1.07 |
| Dimethylformamide, Isophorone | 1.31 |
| Dimethylacetamide | 1.30 |
| Dimethylacetamide, Acetophenone | 1.34 |
| Propylene glycol methyl ether | 1.25 |
| Propylene glycol methyl ether, Isobutanol | 1.33 |
| Dimethylacetamide, Diisobutyl ketone | 1.20 |
| Dimethylacetamide, 2-methyl pyrrolidone | 1.34 |
| Diacetone alcohol | 1.23 |

TABLE 6

Ineffective Agents For Separating Cyclohexane From Cyclohexene By Extractive Distillation

| | |
|---|---|
| Dimethylsulfoxide | Dimethylformamide |
| Isophorone | Ethylene glycol ethyl ether |
| 2-Heptanone | Mesityl oxide |
| 2-Ethyl butanol | 2,6-Dimethyl-4-heptanol |
| n-Decanol | Propionic acid |
| Acetic acid | Hexanoic acid |
| n-Amyl alcohol | 2-Butanol |
| 2-Methyl-1-butanol | 3-Methyl-1-butanol |
| Butyl ether | 3-Pentanone |
| 4-Methyl-2-pentanone | 2-Pentanone |
| Anisole | Methyl isoamyl ketone |
| Ethyl acetate | n-Amyl acetate |
| n-Butyl acetate | Isobutyl acetate |
| 4-Methyl pentyl acetate | Ethylene glycol methyl ether acetate |
| Isobornyl acetate | Methyl valerate |
| Propyl butyrate | Isobutyl isobutyrate |
| n-Hexyl formate | Butyl butyrate |

TABLE 7

Data From Run Made In Rectification Column - Cyclohexane From Cyclohexene By Extractive Distillation

| Agent | Column | Time hrs. | Weight % Cyclohexane | Weight % Cyclohexene | Relative Volatility |
|---|---|---|---|---|---|
| Diacetone alcohol | Overhead | 1 | 60.3 | 39.7 | 1.23 |
|  | Bottoms |  | 25.6 | 74.4 |  |
| Diacetone alcohol | Overhead | 2 | 64.2 | 35.8 | 1.26 |
|  | Bottoms |  | 24.8 | 75.2 |  |

SUMMARY OF THE INVENTION

The objects of the invention are provided by a process for separating cyclohexane from cyclohexene which entails the use of certain oxygenated and nitrogenous organic compounds as the agent in extractive or azeotropic distillation.

DETAILED DESCRIPTION OF THE INVENTION

I have discovered that certain oxygenated organic compounds will effectively enhance the relative volatility of cyclohexane to cyclohexene when employed as the agent in azeotropic distillation. Table 2 lists the compounds that I have found to be effective as azeotrope formers. They are ethanol, n-propanol, n-butanol and ethylene glycol methyl ether.

Table 3 lists several organic compounds that might have been expected to be effective but which were not.

n-Butanol, whose relative volatility had been determined in a vapor-liquid equilibrium still and reported in Table 2 as being effective, was then evaluated in a glass perforated plate rectification column possessing 7.3 theoretical plates. The results are listed in Table 4 and show that n-butanol gave a relative volatility of 2.0.

I have discovered that certain oxygenated and nitrogenous organic compounds will effectively enhance the relative volatility of cyclohexane to cyclohexene by rectification when employed as the agent in extractive distillation. Table 5 lists the compounds that I have found to be effective in extractive distillation. They are isophorone, dimethylformamide, dimethylacetamide, acetophenone, propylene glycol methyl ether, isobutanol, diisobutyl ketone, 2-methyl pyrrolidone and diacetone alcohol.

Table 6 lists a number of organic compounds that might have been expected to be effective but which were not.

Diacetone alcohol, whose relative volatility had been determined in a vapor-liquid equilibrium still and reported in Table 5 as being effective, was then evaluated in a glass perforated plate rectification column possessing 7.3 theoretical plates. The results are listed in Table 7 and show that diacetone alcohol gave a relative volatility of 1.26.

THE USEFULNESS OF THE INVENTION

The usefulness or utility of this invention can be demonstrated by referring to the data presented in Table 1-7. All of the successful azeotropic or extractive agents show that cyclohexane can be separated from cyclohexene by means of azeotropic or extractive distillation in a rectification column and that the ease of separation as measured by relative volatility is considerable. Without these azeotropic or extractive agents, only a very slight improvement will occur in a rectification column. The relative volatility of these two is only 1.07. The data also show that the most attractive agents will operate at a boilup rate low enough to make this a useful and efficient method of recovering high purity cyclohexane from cyclohexene. The stability of the compounds used and the boiling point difference is such that complete recovery and recycle is obtainable by a simple solvent extraction or distillation and the amount required for make-up is small.

WORKING EXAMPLES

Example 1

Thirty grams of cyclohexane, ten grams of cyclohexene and 20 grams of ethylene glycol methyl ether were charged to an Othmer type vapor-liquid equilibrium still and refluxed for five hours. Analysis by gas chromatography gave a vapor composition of 67.5% cyclohexane, 32.5% cyclohexene; a liquid composition of 47.1% cyclohexane, 52.9% cyclohexene which is a relative volatility of 2.33.

Example 2

A glass perforated plate rectification column was calibrated with m-xylene and o-xylene which possesses a relative volatility of 1.11 and found to have 7.3 theoretical plates. A solution comprising 300 grams of cyclohexane, 100 grams of cyclohexene and 100 grams of n-butanol was placed in the stillpot and heated. After four hours of operation at total reflux, the overhead and bottoms samples of approximately two ml. were collected and analysed by gas chromatography. The overhead analysis was 61.4% n-butanol, 34.8% cyclohexane and 3.8% cyclohexene. The bottoms analysis was 4.4% n-butanol, 5.2% cyclohexane and 90.4% cyclohexene. Using these compositions in the Fenske equation with the number of theoretical plates in the column being 7.3, gave an average relative volatility of 2.0 for each theoretical plate. The amount of n-butanol to cyclohexane-cyclohexene in the azeotrope is 61.4 to 38.6. This run is presented in Table 4.

Example 3

Thirty grams of cyclohexane, ten grams of cyclohexene and 20 grams of propylene glycol methyl ether were charged to the vapor-liquid equilibrium still and refluxed for four hours. Analysis gave a vapor composition of 75.8% cyclohexane, 24.2% cyclohexene; a liquid composition of 71.5% cyclohexane, 28.5% cyclohexene which is a relative volatility of 1.25.

Example 4

A solution comprising 75 grams of cyclohexane and 200 grams of cyclohexene was placed in the stillpot of the glass perforated plate rectification column and heated. When refluxing began, an extractive agent comprising diacetone alcohol was pumped into the column at a rate of 15 ml/min. The boilup rate was 20 ml/min. and the temperature of the extractive agent as it entered the column was 85° C. After establishing the feed rate of the extractive agent, the heat input to the cyclohexane-cyclohexene in the stillpot was adjusted to give a total reflux rate of 30-40 ml/min. After two hours of operation, two ml. samples were collected and analysed. The overhead analysis was 64.2% cyclohexane, 35.8% cyclohexene and the bottoms analysis was 24.8% cyclohexane, 75.2% cyclohexene which is a relative volatility on each theoretical plate of 1.26. This run is presented in Table 7.

I claim:

1. A method for recovering cyclohexane from a mixture of cyclohexane and cyclohexene which comprises distilling a mixture of cyclohexane and cyclohexene in the presence of an azeotrope forming agent, recovering the cyclohexane and the azeotrope forming agent as overhead product and obtaining the cyclohexene from the still pot, wherein said azeotrope forming agent comprises one material selected from the group consisting of ethanol, n-propanol, n-butanol and ethylene glycol methyl ether.

2. A method for recovering cyclohexane from a mixture of cyclohexane and cyclohexene which comprises distilling a mixture of cyclohexane and cyclohexene in the presence of about one part of an extractive agent per part of cyclohexane-cyclohexene mixture, recovering the cyclohexane as overhead product and obtaining the cyclohexene and the extractive agent from the stillpot, wherein said extractive agent comprises at least one material selected from the group consisting of isophorone, dimethylformamide, dimethylacetamide, acetophenone, propylene glycol methyl ether, isobutanol, diisobutyl ketone and diacetone alcohol.

* * * * *